(12) United States Patent
Tam et al.

(10) Patent No.: US 10,682,184 B2
(45) Date of Patent: Jun. 16, 2020

(54) TISSUE SAMPLING SYSTEM

(71) Applicants: Siemens Healthcare GmbH, Erlangen OT (DE); Board of Regents, The University of Texas System, Austin, TX (US)

(72) Inventors: Alda Lui Tam, Houston, TX (US); Gouthami Chintalapani, Katy, TX (US)

(73) Assignees: Siemens Healthcare GmbH, Erlangen (DE); Board of Regents, University of Texas, Austin, TX (US)

( * ) Notice: Subject to any disclaimer, the term of this patent is extended or adjusted under 35 U.S.C. 154(b) by 930 days.

(21) Appl. No.: 15/138,536

(22) Filed: Apr. 26, 2016

(65) Prior Publication Data
US 2017/0304008 A1 Oct. 26, 2017

(51) Int. Cl.
*A61B 34/20* (2016.01)
*A61B 6/03* (2006.01)
(Continued)

(52) U.S. Cl.
CPC .............. *A61B 34/20* (2016.02); *A61B 6/032* (2013.01); *A61B 10/0283* (2013.01); *G06T 7/11* (2017.01); *G06T 7/73* (2017.01); *G06T 7/97* (2017.01); *A61B 34/30* (2016.02); *A61B 2010/045* (2013.01); *A61B 2034/2065* (2016.02);
(Continued)

(58) Field of Classification Search
CPC .......... A61B 10/0283; A61B 2010/045; A61B 2034/2065; A61B 34/20; A61B 34/30; A61B 6/032; G06T 2207/10081; G06T 2207/30096; G06T 7/11; G06T 7/73; G06T 7/97

See application file for complete search history.

(56) References Cited

U.S. PATENT DOCUMENTS 7,245,958 B1 7/2007 Navab et al.
8,348,861 B2 1/2013 Glozman et al.
(Continued)

OTHER PUBLICATIONS

Wirz, Raul et al. "An Experimental Feasibility Study on Robotic Endonasal Telesurgery", Concepts, Innovations and Techniques, Congress of Neurological Surgeons, vol. 76, No. 4, Apr. 2015, (pp. 479-484, 6 total pages).
(Continued)

*Primary Examiner* — Michael T Rozanski

(57) ABSTRACT

A system includes acquisition of a three-dimensional image based on at least two two-dimensional images, identification of a tumor based on the three-dimensional image, identification of sub-volumes of the tumor, determination of a first two or more tissue sampling locations based on the sub-volumes, determination of a first tissue sampling device entry point and a first one or more device trajectories associated with the first entry point based on the first tissue sampling locations, movement of a tissue sampling device into the patient volume through patient skin at the first entry point, and movement of the device along the first one or more device trajectories to acquire tissue samples from the first tissue sampling locations, wherein the tissue samples are acquired from the first tissue sampling locations between entry of the device at the first entry point and removal of the device from the first entry point.

15 Claims, 5 Drawing Sheets

(51) Int. Cl.
  *G06T 7/00*    (2017.01)
  *A61B 10/02*   (2006.01)
  *A61B 34/30*   (2016.01)
  *A61B 10/04*   (2006.01)
  *G06T 7/11*    (2017.01)
  *G06T 7/73*    (2017.01)
  *A61B 90/00*   (2016.01)

(52) U.S. Cl.
  CPC ... *A61B 2090/367* (2016.02); *A61B 2090/374* (2016.02); *A61B 2090/376* (2016.02); *G06T 2207/10081* (2013.01); *G06T 2207/30096* (2013.01)

(56) References Cited

U.S. PATENT DOCUMENTS

| | | |
|---|---|---|
| 8,663,130 B2 | 3/2014 | Neubach et al. |
| 2010/0262079 A1 | 10/2010 | Davis et al. |
| 2013/0223702 A1* | 8/2013 | Holsing ............. A61B 5/113 382/128 |
| 2014/0276586 A1 | 9/2014 | Swaney et al. |

OTHER PUBLICATIONS

Swaney, Philip J. et al. "Tendons, Concentric Tubes, and a Bevel Tip: Three Steerable Robots in One Transoral Lung Access System", IEEE Int. Conf. Robert Autom. Author Manuscript, May 2015, DOI: 10.1109/ICRA.2015.7139950, (pp. 5378-5383, 17 total pages).

York, Peter A. et al. "A Wrist for Needle-Sized Surgical Robots", IEEE Int. Conf. Robert Autom. Author Manuscript, May 2015, DOI: 10.1109/ICRA.2015.7139428, (pp. 1776-1781, 21 total pages).

Patil, Sachin et al. "Needle Steering in 3-D via Rapid Replanning", IEEE Transactions on Robotics, vol. 30, No. 4, Aug. 2014, DOI: 10.1109/TRO.2014.2307633, (pp. 853-864, 12 total pages).

Torabi, Meysam et al. "Compact Robotically Steerable Image-Guided Instrument for Multi-Adjacent-Point (MAP) Targeting", IEEE Transactions on Robotics, vol. 30, No. 4, Aug. 2014, DOI: 10.1109/TRO.2014.2304773, (pp. 802-815, 14 total pages).

* cited by examiner

TISSUE SAMPLING SYSTEM

BACKGROUND

According to conventional tumor biopsy techniques, a physician punctures a patient's skin with a sampling device (e.g., a needle) and advances the needle toward a subject organ capsule. The physician advances the device along a planned trajectory while viewing images of the advancing device and the surrounding anatomic structures. As specified by the planned trajectory, the device punctures the organ capsule and enters the tissue of a tumor residing therein. A sample of the tumor is obtained and the device is retracted from the patient through the original puncture location.

A single puncture through skin and the organ capsule is desired to minimize risk of bleeding or complication. This approach limits the areas of the tumor which may be sampled, subjecting the resulting tissue biopsy samples to sampling error. Moreover, in the case of a heterogeneous tumor, the acquired tissue samples may fail to reflect the complete or primary genetic composition of the tumor, which may adversely affect the efficacy of any treatment which is prescribed based on the tissue samples.

DETAILED DESCRIPTION

The following description is provided to enable any person in the art to make and use the described embodiments and sets forth the best mode contemplated for carrying out the described embodiments. Various modifications, however, will remain readily apparent to those in the art.

Generally, some embodiments provide an improved system to sample multiple tissue areas. Systems according to some embodiments provide identification of appropriate tissue sampling locations and efficient sampling of tissues from each of the sampling locations with a single entry point of the sampling device into the organ capsule. A tissue sampling device exhibiting multiple degrees of freedom is used in some embodiments to acquire tissue samples from more than one sampling location with one skin puncture.

Figure 1:
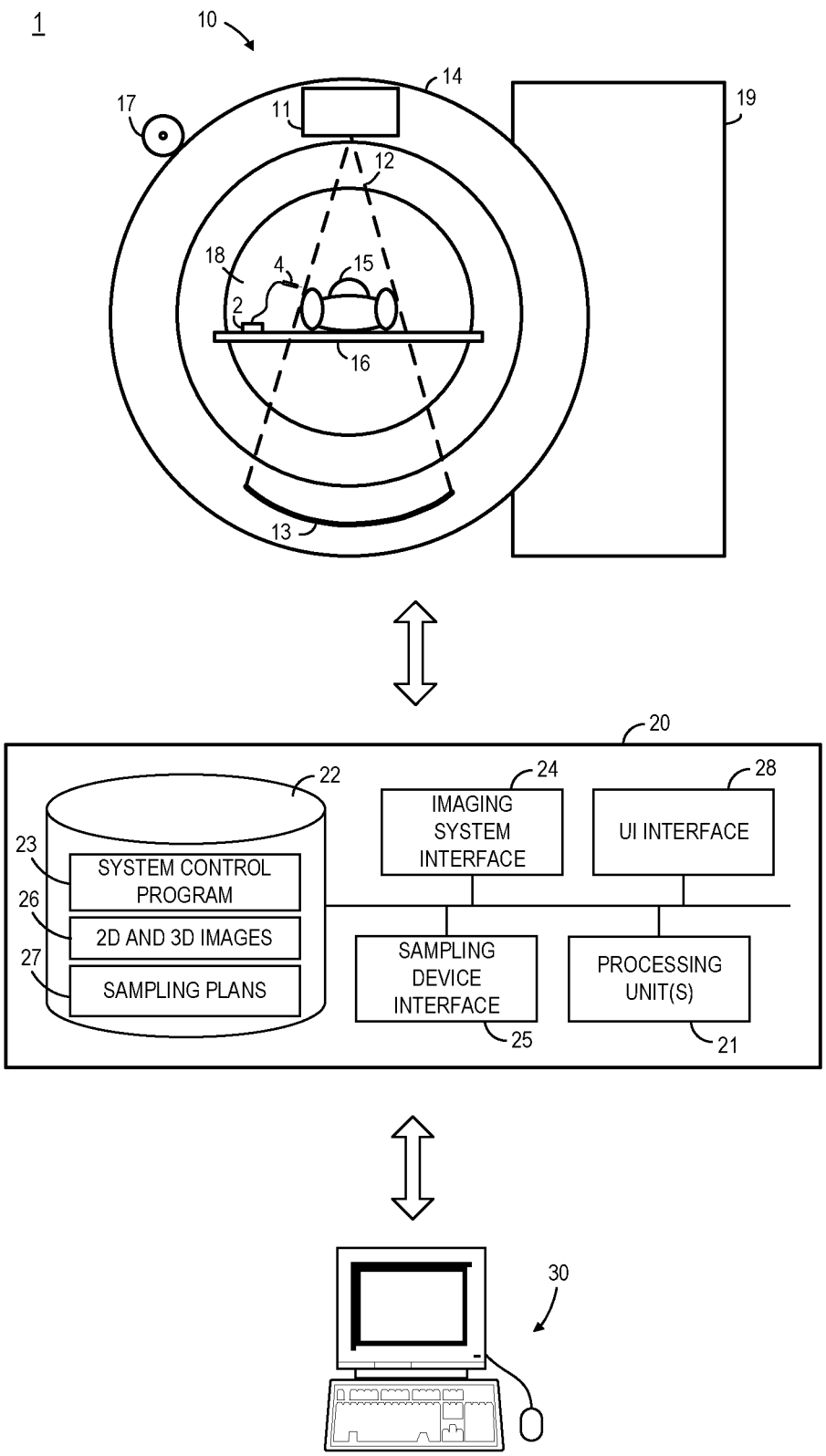
FIG. 1 illustrates a system according to some embodiments.

FIG. 1 illustrates system 1 according to some embodiments. Embodiments are not limited to the elements and/or arrangement of system 1. System 1 includes interventional system 10, control and processing system 20, and operator terminal 30. Generally, and according to some embodiments, interventional system 10 supports insertion of a device into a patient and imaging thereof. Control and processing system 20 controls imaging system 10 and receives the acquired images therefrom. Control and processing system 20 processes the images as described below and provides output to terminal 30 for display thereby. Such processing may be based on user input received by terminal 30 and provided to control and processing system 20 by terminal 30.

Interventional system 10 supports image-guided sampling of patient tissue. Interventional system 10 provide a tissue-sampling device and control mechanisms therefor, and components for acquiring three-dimensional images and/or two-dimensional images which may be used to generate corresponding three-dimensional images using known reconstruction methods.

Interventional system 10 comprises a CT scanner including radiation source 11 emitting corresponding fan-shaped X-ray beam 12 toward opposing radiation detector 13. Radiation source 11 and radiation detector 13 are mounted on gantry 14 such that they may be rotated through 360 degrees while maintaining the same physical relationship therebetween.

Interventional system 10 may comprise any system that is or becomes known, including but not limited to those described below with respect to FIGS. 8 and 9. According to some embodiments, interventional system 10 may comprise an X-ray imaging system, a camera, a magnetic resonance imaging system, or a positron emission tomography scanner.

Radiation source 11 may comprise any suitable radiation source, including but not limited to an X-ray tube. In some embodiments, radiation source 11 emits electron, photon or other type of radiation having energies ranging from 50 to 150 keV.

Radiation detector 13 may comprise any system to acquire an image based on received x-ray radiation. In some embodiments, radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

The charge developed and stored by radiation detector 13 represents radiation intensities at each location of a radiation field produced by x-rays emitted from radiation source 11. The radiation intensity at a particular location of the radiation field represents the attenuation properties of tissues of patient 15 lying along a divergent line between radiation source 11 and the particular location of the radiation field. The set of radiation intensities acquired by radiation detector 13 may therefore represent a two-dimensional projection image of these tissues.

In operation, patient 15 is positioned on bed 16 to place a portion of patient 15 between radiation source 11 and radiation detector 12. Next, radiation source 11 and radiation detector 13 are rotated by rotation drive 17 around cavity 18 in which patient 15 lies. During this rotation, radiation source 11 is powered by high-voltage generator 19 to transmit x-ray radiation toward detector 13. Detector 13 receives the radiation and produces a set of data (i.e., a projection image) for each projection angle. Embodiments are not limited to CT scanners.

Base unit 2 may comprise any suitable system to support insertable/injectable tissue sampling device 4. Base unit 2 may be mounted on any component of system 10, and system 10 may comprise more than one base unit 2 and associated device 4. In some embodiments, one base unit 2 may control and/or be coupled to more than one tissue sampling device 4. According to some embodiments, base unit 2 may comprise an articulated robot (e.g., a robotic arm) which holds and advances device 4 as described herein, for example, but not limited to, a KUKA LWR (Light Weight Robot).

Device 4 may comprise a needle (e.g., solid or hollow, beveled or conical), one or more opposing jaws, a curette, or any other tissue sampling device that is or becomes known. In some embodiments, device 4 is not transparent to the imaging modality used by system 10 and therefore appears in any images acquired thereby. Insertion/injection of device 4 may be controlled by a physician or other qualified operator.

System 20 may comprise any general-purpose or dedicated computing/controller system. Accordingly, system 20 includes one or more processors 21 configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. One or more processing units 21 may execute system control program 23 to move device 18 along a planned trajectory and to acquire tissue samples. Control program 23 may include a mathematical framework to compute optimal trajectories for tissue sampling. Control program 23 may also be executed to move gantry 14, to cause radiation source 11 to emit radiation, and to control detector 13 to acquire images 26. In this regard, system 20 includes imaging system interface 24 and device interface 25 for communication with system 10. According to some embodiments, interface 24 supports Advanced X.25 Connection Services (AXCS) messages and interface 25 comprises an examination control console and joystick.

Acquired images 26 may be stored in data storage device 22 in DICOM or another data format. Each acquired image 26 may be further associated with details of its acquisition, including but not limited to imaging plane position and angle, imaging position, radiation source-to-detector distance, patient anatomy imaged, patient position, x-ray tube voltage, image resolution and radiation dosage.

Images 26 may include three-dimensional images generated by system control program 23 based on two or more of two-dimensional images 26. The three-dimensional images 26 may be used to identify tissue regions of interest and plan device trajectories as described herein.

UI interface 28 may receive input from terminal 30, which may be used to control device 4, the acquisition of images, identification of regions of interest. Terminal 30 may simply comprise a display device and an input device coupled to system 20. In some embodiments, terminal 30 is a separate computing device such as, but not limited to, a desktop computer, a laptop computer, a tablet computer, and a smartphone.

Each of system 10, system 20 and terminal 30 may include other elements which are necessary for the operation thereof, as well as additional elements for providing functions other than those described herein.

According to the illustrated embodiment, system 20 controls the elements of system 10. System 20 also processes images received from system 10. Embodiments are not limited to a single system performing each of these functions. For example, system 10 may be controlled by a dedicated control system, with the acquired images being provided to a separate image processing system over a computer network or via a physical storage medium (e.g., a DVD).

Figure 2:
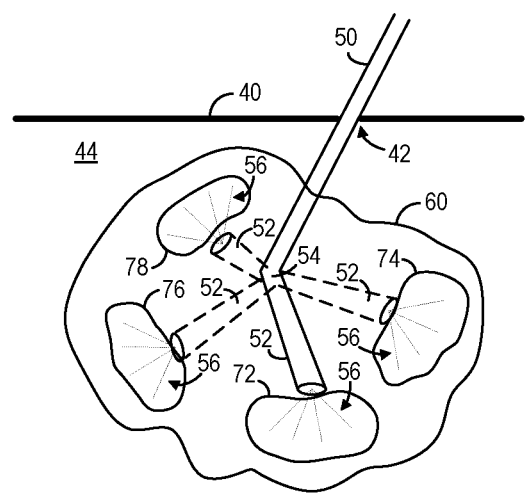
FIG. 2 is an illustration of tissue sampling according to some embodiments.

FIG. 2 is a representational illustration of tissue sampling according to some embodiments. Device 50 punctures patient skin 40 to create hole/path 42 through which device 50 passes. Device 50 thereby enters patient internal volume/organs 44 and proceeds to enter volume of interest 60, which may be a tumor. Device 50 may comprises a needle, a concentric tube robot, or any other tissue sampling device that is or becomes known and which is capable of performing the functions described herein.

In the illustrated embodiment, device 50 includes lower portion 52 which is coupled to an upper portion via hinge 54. Hinge 54 may comprise any structure allowing relative angular movement of lower portion 52 with respect to the upper portion. Embodiments are not limited to a device 50 comprising a hinge.

As illustrated by solid lines, lower portion 52 may be positioned so as to acquire tissue samples from tissue volume 72. The dotted representations of lower portion 52 further indicate that lower portion 52 may be positioned to also acquire tissue samples from variously-located tissue volumes 74, 76 and 78. The movement and positioning of lower portion 52 to acquire tissue samples at various locations of tumor 60 may be facilitated by hinge 54 in some embodiments, and by other mechanisms in other embodiments. The different volumes and locations from which to acquire tissue may be determined based on prior image-based segmentation of tumor 60, as will be described in detail below. The needle path 50 and 52 and the angle at which to intercept the skin entry point may be determined based on an optimization algorithm such that maximum tissue samples can be collected from the tumor, as will be described in detail below.

According to some embodiments, the tissue acquisitions from tissue volumes 72 through 78 may occur without having to remove device 50 from hole 42 between successive tissue acquisitions. In other words, tissue is acquired from multiple locations of volume 60 using a single puncture of patient skin 40.

Tissue may be acquired according to some embodiments by one or more of a needle, a cannula, a vise grip, a vacuum, and/or any other device that is or becomes known. Dotted lines 56 of FIG. 2 illustrate four tissue acquisitions within each volume 72 through 78 corresponding to a single location of lower portion 52. The four tissue acquisitions may be performed by a single structure which projects from lower portion 52, or lower portion 52 may include more than one (e.g., two, four) devices which may project therefrom to acquire tissue samples.

Figure 3:
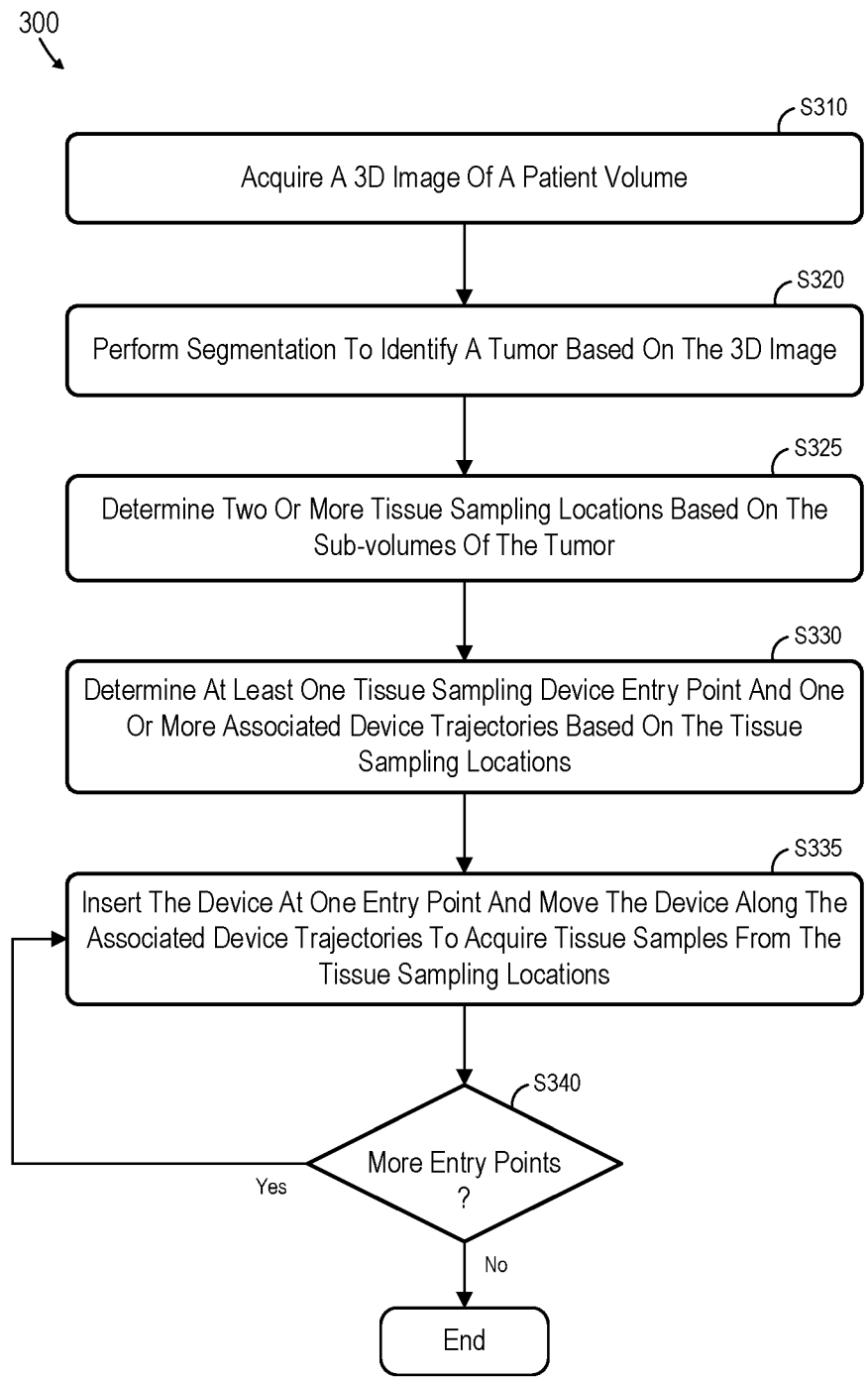
FIG. 3 is a flow diagram of a process according to some embodiments.

FIG. 3 comprises a flow diagram of process 300 according to some embodiments. Process 300 and the other processes described herein may be performed using any suitable combination of hardware, software or manual systems. Software embodying these processes may be stored by any non-transitory tangible medium, including a fixed disk, a floppy disk, a CD, a DVD, a Flash drive, or a magnetic tape. According to some embodiments, some or all of the steps of process 300 are embodied within executable code of system control program 23 and executed by processing unit(s) 21 of device 20.

Initially, a three-dimensional image is acquired at S310. The three-dimensional image may be acquired using an imaging system which acquires three-dimensional images or a system which generates three-dimensional images based on acquired two-dimensional images. For example, S310 may include acquiring at least two two-dimensional images of a patient within a short timeframe so that they each represent a state of the patient within the timeframe. With reference to FIG. 1, radiation source 11 and detector 13 may operate to acquire a first two-dimensional image while in a first position. Next, gantry 14 is rotated so that source 11 and detector 13 are in different positions relative to patient 15, and a second two-dimensional image is acquired. Any number of two-dimensional images may be acquired, and at least two of the images are acquired at least 30 degrees apart from one another.

A three-dimensional image may be generated from the acquired two-dimensional images using any technique that is or becomes known, including but not limited to back-projection, Feldkamp-Davis-Kressman (FDK), and/or other reconstruction techniques. Embodiments may employ any imaging modality to generate a three-dimensional image at S310 (e.g., magnetic resonance imaging, ultrasound imaging, molecular imaging), including modalities which do not require prior acquisition of two-dimensional images.

A tumor (or other tissue of interest) is identified based on the three-dimensional image at S320 using any technique that is or becomes known. Identification of the tumor may be based on additional three-dimensional and two-dimensional images, and/or may incorporate user input. In one example, the three-dimensional image is displayed on terminal 30 and a user uses an input device to denote the three-dimensional contours of the tumor, to drop a seed point within the tumor, to draw a line through the tumor, etc.

The tumor may be further divided into subvolumes based on the geometry and heterogeneity of the tumor from the images using known algorithms and/or manual steps. In some embodiments, the sub-volumes identify portions of the tumor which differ in one or more characteristics. The sub-volumes may therefore identify heterogeneities in the tumor. According to some embodiments, different types of tissue are portrayed differently in the three-dimensional image (e.g., different color, different shading, etc.) and therefore the different sub-volumes may be identified at S320 based on image processing techniques.

Two or more tissue sampling locations are determined at S325, based on the identified sub-volumes. The sampling locations may be determined as the center of each subvolume. The sampling locations may be determined so as to maximize the heterogeneity of the samples acquired from the tumor. For example, if each identified sub-volume is associated with a particular type of tissue (as determined by segmentation at S320) than the tissue sampling locations are determined such that at least one sample is acquired of each type of tissue. The determined sampling locations may be displayed to the operator on the user interface.

Once the tumor is segmented and the subvolumes computed, the user may be asked to confirm the sampling locations. The user may have the opportunity to re-draw/adjust the subvolumes and sampling locations in some embodiments.

Based on the tissue sampling locations, at least one tissue sampling device entry point and one or more associated device trajectories are determined at S330. The device entry point and device trajectories are determined such that a device entering the patient at the entry point and following the one or more trajectories would be able to acquire a tissue sample at each of the determined two or more tissue sampling locations. The determination at S330 may include a mathematical formulation to optimize the needle path and the skin entry angle between 50 and 40 such that tissue samples can be collected from at least two or more locations within the tumor (72, 74, 76 and 78).

Determination of the device entry point and one or more associated device trajectories may depend upon, at least, the location and type of structures and/or tissue between the patient's skin and the sampling locations, and the degrees of freedom and movement capabilities provided by the sampling device. For example, a particular entry point and set of sampling locations may require a complex trajectory to avoid bone or a sensitive tissue structure. If the device is not capable of moving along such a trajectory, then another entry point may be determined. In some instances, two or more entry points and associated trajectories may be required due to the locations of intervening structures and/or limitations in the maneuverability of the sampling device. The user may also provide a potential region for the skin entry point to constrain the mathematical formulation of the trajectories.

Flow may pause after S330, until the patient is positioned for tissue sampling. For example, the at least two two-dimensional images may be acquired at a particular time and date. A later-conducted planning stage may consist of identification and segmentation of the tumor and determination of one or more entry points and one or more associated device trajectories. Still later, on another scheduled date, a patient may arrive at a medical facility for execution of the remainder of process 300.

The patient may be positioned on table 16 and registered with reference images as is known in the art. Additional images may be acquired to determine whether the patient position and position of internal volumes conforms sufficiently to positions assumed by the determined entry points and trajectories. If not, the patient may be repositioned and/or the entry points and trajectories may be re-determined to account for non-conformities. Additionally, the base 2 and device 4 may be positioned next to the patient and registered to the patient 15 and the imaging system 10 using reference markers or images.

At S335, an operator may operate base unit 2 to insert device 4 into the patient at one of the determined entry points. The operator may perform a control check to make sure the device 4 is aligned with the computer-planned needle trajectory before advancing the needle any further. Base unit 2 may be operated using a displayed user interface and/or via manual controls (e.g., a joystick or other manual control). After insertion at the entry point, the operator controls device 4 to move the device along the device trajectories which are associated with the entry point and to acquire at least one tissue sample along each trajectory. Images of the patient and device 4 internal to the patient may be acquired and viewed during insertion and movement along the device trajectories in order to assist/guide the movement. The desired trajectories may be displayed along with the acquired images in this regard. Any modifications of the trajectories may be permitted during the advancement of the needle based on the most recently-obtained imaging.

Any suitable mechanism and method of device control may be utilized at S335. The mechanism and method are typically dependent upon the physical arrangement of the tissue sampling device used. According to some embodiments, a hollow device is inserted at the entry point at a particular angle and to a particular depth, and remains in this position while a tissue sampling structure disposed within the hollow is manipulated to move along the device trajectories.

FIGS. 4 through 7 are views of tissue sampling devices according to some embodiments. Some embodiments may employ any other suitable sampling devices which are or become known.

Figure 4:
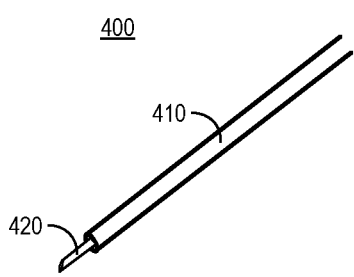
FIG. 4 is a view of a tissue sampling device according to some embodiments.

FIG. 4 illustrates device 400 which includes tube 410 and bevel-tipped needle 420. Tube 410 may be bendable prior to insertion, and needle 420 may be fully or partially hollow. In the latter regard, needle 420 may be coupled to a vacuum system to facilitate tissue extraction. Is some embodiments, needle 420 is curved to facilitate trajectories which are not linear with tube 410. The bevel tip may also allow a range of curved trajectories as is known in the art. In some embodiments, tube 410 and needle 420 may comprise a cannula (or catheter) and a stylet, respectively, such as, but not limited to, a cannula and stylet of a device as described in Torabi et al., *Compact Robotically-Steerable Image-Guided Instrument for Multi-Adjacent-Point (MAP) Targeting*, IEEE Transactions on Robotics, Vol. 30, No. 4, August 2014.

In a case that needle 420 is flexible, it may be steered along a straight or curved trajectory by maneuvering its base. As is known in the art, the needle base may, using real-time imaging, be robotically manipulated based on a virtual spring model, path planning, needle tip and profile detection and an iterative estimation of tissue stiffness by analyzing the displacement of the tissue along the length of the needle as a result of forces applied by the needle on the tissue. Similar techniques may be employed to guide any of the tissue sampling devices mentioned herein.

Figure 5:
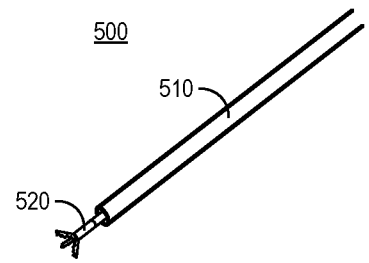
FIG. 5 is a view of a tissue sampling device according to some embodiments.
Figure 6:
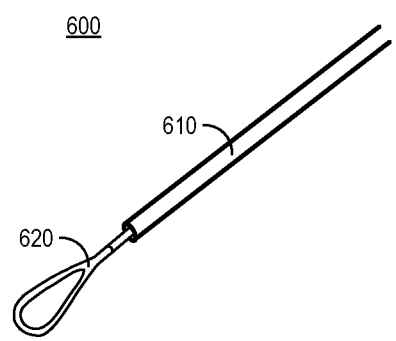
FIG. 6 is a view of a tissue sampling device according to some embodiments.

FIG. 5 illustrates device 500 consisting of tube 510 and gripper unit 520. Base unit 2, for example, may allow an operator to activate jaws of gripper unit 520 to close upon and extract a tissue sample. Device 600 of FIG. 6 includes tube 610 and curette 620 for cutting tissue. Either of gripper unit 520 and curette 620 may also be coupled to a vacuum system in some embodiments.

Figure 7:
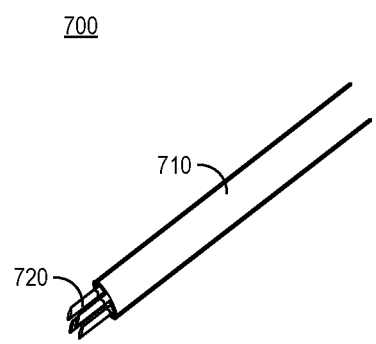
FIG. 7 is a view of a tissue sampling device according to some embodiments.

FIG. 7 illustrates device 700 including tube 710 and multiple sampling devices 720. As illustrated, devices 720 include needles which may be similar to needle 420. In this regard, a tissue sampling device according to some embodiments may include more than one of the tissue sampling mechanisms described herein or otherwise known.

A tube such as tubes 410, 510, 610 and 710 may be telescopic according to some embodiments. In such a case, the illustrated portion is a last and thinnest segment of the tube. The component tubes of such an arrangement may be pre-curved to increase control and accuracy.

Returning to process 300, it is determined at S340 whether additional entry points were determined at S330. If so, flow returns to S335 to insert the device at a next entry point and to then move the device along determined trajectories associated with the next entry point. Flow therefore cycles between S335 until all entry points have been processed.

Figure 8:
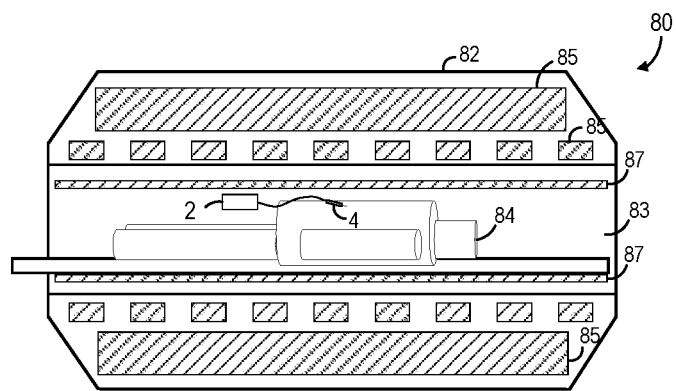
FIG. 8 illustrates a system according to some embodiments.
Figure 9:
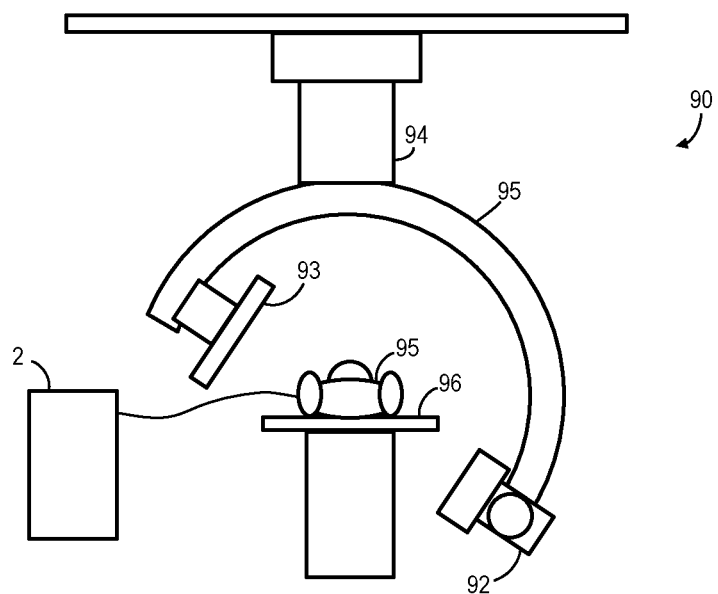
FIG. 9 illustrates a system according to some embodiments.

FIGS. 8 and 9 illustrate other implementations of the systems described above. Embodiments are not limited to the systems depicted herein. Embodiments of base unit 2 and device 4 may be configured for selective coupling and uncoupling to an imaging device, and/or for use in conjunction with multiple instances of base unit 2 and device 4.

System 80 of FIG. 8 illustrates MRI system 80 according to some embodiments. MRI system 80 includes MRI chassis 82, which defines bore 83 in which patient 84 is disposed. MRI chassis 82 includes polarizing main magnet 85, gradient coils 86 and RF coil 87 arranged about bore 83. According to some embodiments, polarizing main magnet 85 generates a uniform main magnetic field (B0) and RF coil 87 emits an excitation field (B1).

Gradient coils 86 produce magnetic field gradients Gx, Gy, and Gz which are used for position-encoding NMR signals. RF coil 87 both emits radio-frequency pulses and scans the alternating field which is produced as a result of processing nuclear spins, i.e. the nuclear spin echo signals. The received signals are received and an image is reconstructed therefrom according to known techniques.

Base unit 2 may be mounted within MRI system 80 (e.g., within core 83) and may control the insertion and subsequent trajectories of device 4 as described above.

System 90 of FIG. 9 includes floor-mounted base unit 2, and also includes radiation source 92 and radiation detector 93. Source 92 and detector 93 are mounted to c-arm 95, which is configured to translate with respect to support 94. Translation of c-arm 95 facilitates acquisition of two-dimensional images from various projection angles.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
an imaging system to:
acquire image data of a patient volume; and
a processor to:
generate a three-dimensional image of the patient volume based on the image data;
identify a tumor based on the three-dimensional image;
identify two or more heterogeneous sub-volumes of the tumor, the two or more heterogeneous sub-volumes differing from one another in one or more characteristics;
determine a first two or more non-adjacent tissue sampling locations based on the sub-volumes, at least two of the first two or more non-adjacent tissue sampling locations located at different ones of the two or more sub-volumes; and
determine a first tissue sampling device entry point and a first two or more device trajectories associated with the first tissue sampling device entry point based on the first two or more non-adjacent tissue sampling locations; and
a tissue sampling device to:
enter the patient volume at the first tissue sampling device entry point;
move along the first two or more device trajectories to acquire tissue samples from each of the first two or more non-adjacent tissue sampling locations,
wherein the tissue samples are acquired from each of the first two or more non-adjacent tissue sampling locations after entry of the tissue sampling device at the first tissue sampling device entry point and before removal of the tissue sampling device from the first tissue sampling device entry point.

2. A system according to claim 1,
the processor to:
determine a second two or more non-adjacent tissue sampling locations based on the sub-volumes, at least two of the first two or more non-adjacent tissue sampling locations located at different ones of the two or more sub-volumes; and
determine a second tissue sampling device entry point and a second two or more device trajectories associated with the second tissue sampling device entry point based on the second two or more non-adjacent tissue sampling locations; and the tissue sampling device to:
enter the patient volume at the second tissue sampling device entry point;
move along the second two or more device trajectories to acquire tissue samples from the second two or more non-adjacent tissue sampling locations,
wherein the tissue samples acquired from the second two or more non-adjacent tissue sampling locations are acquired before entry of the tissue sampling device at the second tissue sampling device entry point and after removal of the tissue sampling device from the second tissue sampling device entry point.

3. A system according to claim 1,
wherein the tissue sampling device comprises a concentric tube robot.

4. A system according to claim 3,
wherein the tissue sampling device comprises a needle.

5. A system according to claim 4,
wherein the tissue sampling device comprises a hollow needle and a vacuum device to generate a vacuum within the hollow needle.

6. A method comprising:
acquiring a three-dimensional image of a patient volume;
identifying a tumor based on the three-dimensional image;
identifying two or more heterogeneous sub-volumes of the tumor, the two or more heterogeneous sub-volumes differing from one another in one or more characteristics;
determining a first two or more non-adjacent tissue sampling locations based on the sub-volumes, at least two of the first two or more non-adjacent tissue sampling locations located at different ones of the two or more sub-volumes;
determining a first tissue sampling device entry point and a first two or more device trajectories associated with the first tissue sampling device entry point based on the first two or more non-adjacent tissue sampling locations;
moving a tissue sampling device into the patient volume through patient skin at the first tissue sampling device entry point; and
moving the tissue sampling device along the first two or more device trajectories to acquire tissue samples from each of the first two or more non-adjacent tissue sampling locations,
wherein the tissue samples are acquired from each of the first two or more non-adjacent tissue sampling locations between entry of the tissue sampling device at the first tissue sampling device entry point and removal of the tissue sampling device from the first tissue sampling device entry point.

7. A method according to claim 6, further comprising:
determining a second two or more non-adjacent tissue sampling locations based on the sub-volumes;
determining a second tissue sampling device entry point and a second two or more non-adjacent device trajectories associated with the second tissue sampling device entry point based on the second two or more non-adjacent tissue sampling locations, at least second two of the two or more non-adjacent tissue sampling locations located at different ones of the two or more sub-volumes;
moving the tissue sampling device into the patient volume through patient skin at the second tissue sampling device entry point; and
moving the tissue sampling device along the second two or more device trajectories to acquire tissue samples from the second two or more non-adjacent tissue sampling locations,
wherein the tissue samples acquired from the second two or more non-adjacent tissue sampling locations are acquired between entry of the tissue sampling device at the second tissue sampling device entry point and removal of the tissue sampling device from the second tissue sampling device entry point.

8. A method according to claim 6,
wherein the tissue sampling device comprises a concentric tube robot.

9. A method according to claim 8,
wherein the tissue sampling device comprises a needle.

10. A method according to claim 9,
wherein the tissue sampling device comprises a hollow needle and a vacuum device to generate a vacuum within the hollow needle.

11. A non-transitory computer-readable medium storing processor-executable program code, the program code executable to cause a computing device to:
acquire a three-dimensional image of a patient volume;
identify a tumor based on the three-dimensional image;
identify two or more heterogeneous sub-volumes of the tumor, the two or more heterogeneous sub-volumes differing from one another in one or more characteristics;
determine a first two or more non-adjacent tissue sampling locations based on the sub-volumes, at least two of the first two or more non-adjacent tissue sampling locations located at different ones of the two or more sub-volumes;
determine a first tissue sampling device entry point and a first two or more device trajectories associated with the first tissue sampling device entry point based on the first two or more non-adjacent tissue sampling locations;
move a tissue sampling device into the patient volume through patient skin at the first tissue sampling device entry point; and
move the tissue sampling device along the first two or more device trajectories to acquire tissue samples from each of the first two or more non-adjacent tissue sampling locations,
wherein the tissue samples are acquired from each of the first two or more non-adjacent tissue sampling locations between entry of the tissue sampling device at the first tissue sampling device entry point and removal of the tissue sampling device from the first tissue sampling device entry point.

12. A medium according to claim 11, the program code further executable to cause a computing device to:
determine a second two or more non-adjacent tissue sampling locations based on the sub-volumes;
determine a second tissue sampling device entry point and a second two or more device trajectories associated with the second tissue sampling device entry point based on the second two or more non-adjacent tissue sampling locations, at least two of the second two or more non-adjacent tissue sampling locations located at different ones of the two or more sub-volumes;

move the tissue sampling device into the patient volume through patient skin at the second tissue sampling device entry point; and move the tissue sampling device along the second two or more device trajectories to acquire tissue samples from the second two or more non-adjacent tissue sampling locations, wherein the tissue samples acquired from the second two or more non-adjacent tissue sampling locations are acquired between entry of the tissue sampling device at the second tissue sampling device entry point and removal of the tissue sampling device from the second tissue sampling device entry point.

13. A medium according to claim 11,
wherein the tissue sampling device comprises a concentric tube robot.

14. A medium according to claim 13,
wherein the tissue sampling device comprises a needle.

15. A medium according to claim 14,
wherein the tissue sampling device comprises a hollow needle and a vacuum device to generate a vacuum within the hollow needle.

\* \* \* \* \*